United States Patent [19]

Johnston et al.

[11] Patent Number: 5,300,782
[45] Date of Patent: Apr. 5, 1994

[54] GAMMA RAY DETECTOR FOR PET SCANNER

[75] Inventors: Brian D. Johnston, Hartland; David L. McDaniel, Dousman; James G. Colsher, Waukesha, all of Wis.

[73] Assignee: General Electric Company, Milwaukee, Wis.

[21] Appl. No.: 904,791

[22] Filed: Jun. 26, 1992

[51] Int. Cl.⁵ .......................... G01T 1/20; G01T 1/202
[52] U.S. Cl. ................................. 250/363.03; 250/366; 250/368
[58] Field of Search ................... 250/363.03, 363.04, 250/366, 367, 368

[56] References Cited

U.S. PATENT DOCUMENTS

| | | | |
|---|---|---|---|
| 4,394,576 | 7/1983 | Mitaka et al. | 250/366 |
| 4,743,764 | 5/1988 | Casey et al. | 250/363 |
| 4,749,863 | 6/1988 | Casey et al. | 250/363 |
| 4,750,972 | 7/1988 | Casey et al. | 156/645 |
| 4,864,138 | 9/1989 | Mullani | 250/363.03 |
| 4,929,835 | 5/1990 | Yamashita et al. | 250/367 |
| 4,945,241 | 7/1990 | Yamashita et al. | 250/367 |
| 5,091,650 | 2/1992 | Uchida et al. | 250/366 |
| 5,227,634 | 7/1993 | Ryuo et al. | 250/366 X |

FOREIGN PATENT DOCUMENTS 62-135787  6/1987  Japan .............................. 250/363.03

OTHER PUBLICATIONS

Yamamoto et al., "A BGO Detector Using a New Encoding Scheme for a High Resolution Positron Emission Tomograph", Nuc. Ins. & Met. in Phy. Rea., A248, 1986, pp. 557–561.

*Primary Examiner*—Constantine Hannaher
*Assistant Examiner*—Edward J. Glick
*Attorney, Agent, or Firm*—Quarles & Brady

[57] ABSTRACT

A PET scanner includes a ring of detector units which receive gamma rays produced by annihilation events. Each detector unit includes a 6×6 array of BGO scintillation crystals mounted in front of a 2×2 array of photomultiplier tubes. The position of a scintillation event within the crystal array is determined more accurately by selectively painting the side surfaces of the array crystals.

6 Claims, 2 Drawing Sheets

GAMMA RAY DETECTOR FOR PET SCANNER

BACKGROUND OF THE INVENTION

The field of the invention is positron emission tomography (PET) scanners, and particularly gamma ray detectors employed to locate and count the positron annihilation events.

Positrons are positively charged electrons which are emitted by radionuclides that have usually been prepared using a cyclotron. The radionuclides most often employed in diagnostic imaging are fluorine-18 (18F), carbon-11 ($^{11}C$), nitrogen-13 ($^{13}N$), and oxygen-15 ($^{15}O$). These are employed as radioactive tracers called "radiopharmaceuticals" by attaching them to substances, such as glucose or carbon dioxide. The radiopharmaceuticals are injected in the patient and become involved in such processes as blood flow, fatty acid and glucose metabolism, and protein synthesis.

As the radionuclides decay, they emit positrons. The positrons travel a very short distance before they encounter an electron, and when this occurs, they are annihilated and converted into two photons, or gamma rays. This annihilation event is characterized by two features which are pertinent to PET scanners—each gamma ray has an energy of 511 keV and the two gamma rays are directed in nearly opposite directions. An image is created by determining the number of such annihilation events at each location within the field of view.

The PET scanner includes one or more rings of detectors which encircle the patient and which convert the energy of each 511 keV photon into a flash of light that is sensed by a photomultiplier tube (PMT). Coincidence detection circuits connect to the detectors and record only those photons which are detected simultaneously by two detectors located on opposite sides of the patient. The number of such simultaneous events indicates the number of positron annihilations that occurred along a line joining the two opposing detectors. Within a few minutes hundreds of millions of events are recorded to indicate the number of annihilations along lines joining pairs of detectors in the ring. These numbers are employed to reconstruct an image using well known computed tomography techniques.

The resolution of the reconstructed image is determined in part by the number and size of the detector elements which encircles the patient. By decreasing the size of each detector and increasing their number, the image resolution is increased, but the cost and complexity of the resulting electronic circuitry is also increased. One method which is used to improve resolution without driving the costs up is to employ a set of separate scintillation crystals of small size with each electronic circuit and encode the signal to indicate which crystal recorded the scintillation event. In U.S. Pat. No. 4,394,576, for example, four separate crystals are employed with two PMTs and the relative magnitudes of the signals detected by the PMTs indicates which of the four crystals recorded the event. A single channel thus produces a crystal address which has four times the resolution of prior detectors that employ one crystal with each PMT. This method is not effective if more than four crystals are used with each pair of PMTS, and in an effort to further improve image resolution, U.S. Pat. Nos. 4,743,764; 4,749,863 and 4,750,972 disclose a structure which employs a single large scintillation crystal with four PMTS. Slots are cut in the large crystal to divide it into separately identifiable segments, and by varying the depth of these slots, the location of the segment in the crystal which recorded the scintillation event can be identified. As many as eight segments in a row can be separately identified using this technique, but it requires the use of large, expensive crystals, and the slots have a thickness which reduces the packing fraction of the detector.

SUMMARY OF THE INVENTION

The present invention relates to an improved detector unit for a PET scanner in which a set of separate scintillation crystals are packed together into a matrix and disposed in front of a plurality of photomultiplier tubes, and in which the abutting surfaces of the crystals are treated to cause the light produced by a scintillation event occurring in one of the crystals to be shared with abutting crystals in varying amounts, such that the relative magnitudes of the signals produced by the photomultiplier tubes will indicate which crystal detected the gamma ray. The abutting crystal surfaces on peripherally located crystals are treated to reflect substantially all the light, others, located inward from the peripheral crystals, are treated to allow a fraction of the light to pass through to the adjacent crystal, and others, located in the central region, are treated to allow substantially all of the light to pass through.

A general object of the invention is to provide a high resolution detector unit using a set of small scintillation crystals. The separate rectangular crystals are tightly packed into a two-dimensional array with their side surfaces in abutment. The abutting side surfaces are treated with paint or the like to encode the location of a scintillation event into the relative magnitudes of the PMT signals. There are no gaps between crystals so that a high packing fraction is achieved.

Another object of the invention is to provide a high resolution detector unit at lower cost. By using separate, relatively small scintillation crystals, rather than a single large crystal, overall detector cost is reduced.

Yet another object of the invention is to provide increased detector resolution. While arrays of separate crystals have been used in prior detector units, reliable location of the scintillation event could not be achieved with arrays of more than four crystals in a row. By treating abutting crystal surfaces according to the present invention, a 6×6 array of thirty-six crystals may be constructed and used successfully with four PMTS.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1:
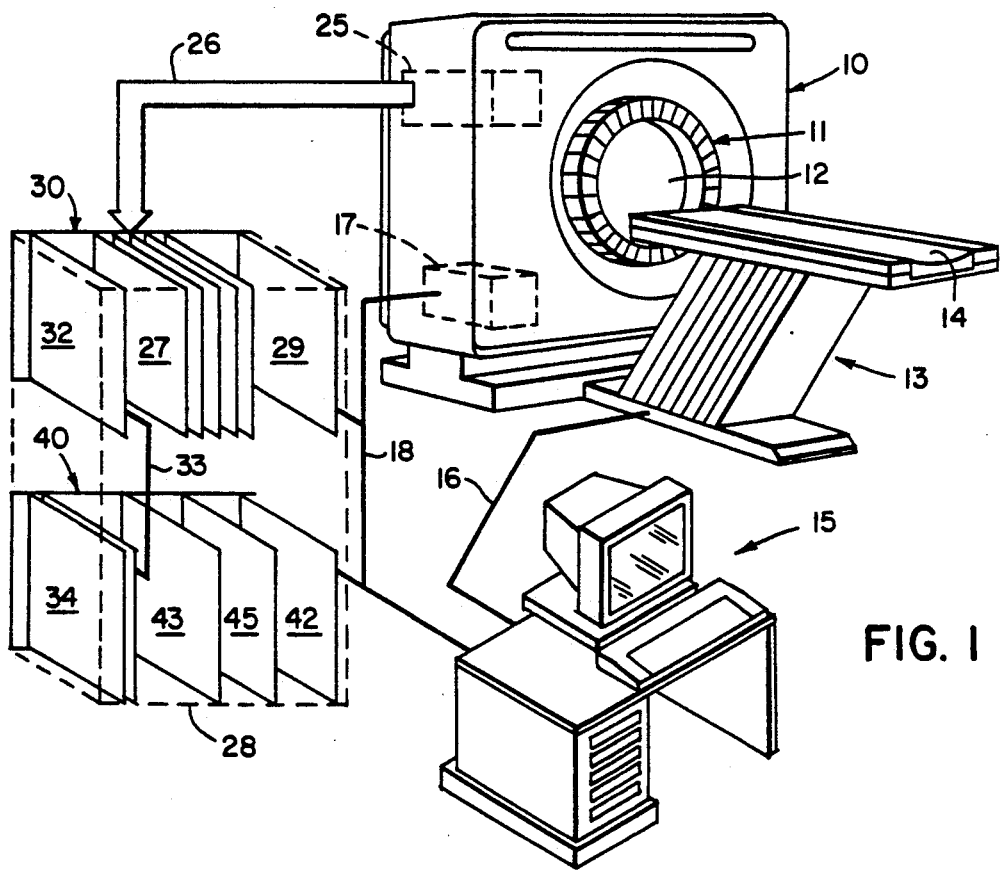
FIG. 1 is a pictorial view with parts cut away of a PET scanner system which employs the present invention.

Referring particularly to FIG. 1, the PET scanner system includes a gantry 10 which supports a detector ring assembly 11 about a central opening, or bore 12. A patient table 13 is positioned in front of the gantry 10 and is aligned with the central axis of the bore 12. A patient table controller (not shown) moves the table bed 14 into the bore 12 in response to commands received from an operator work station 15 through a serial communications link 16. A gantry controller 17 is mounted within the gantry 10 and is responsive to commands received from the operator Fork station 15 through a second serial communication or local area network link 18 to operate the gantry. For example, the gantry can be tilted away from vertical on command from the operator, it can perform a "transmission scan" with a calibrated radionuclide source to acquire attenuation measurements, or it can perform a normal scan in which positron annihilation events are counted and an image produced.

Figure 2:
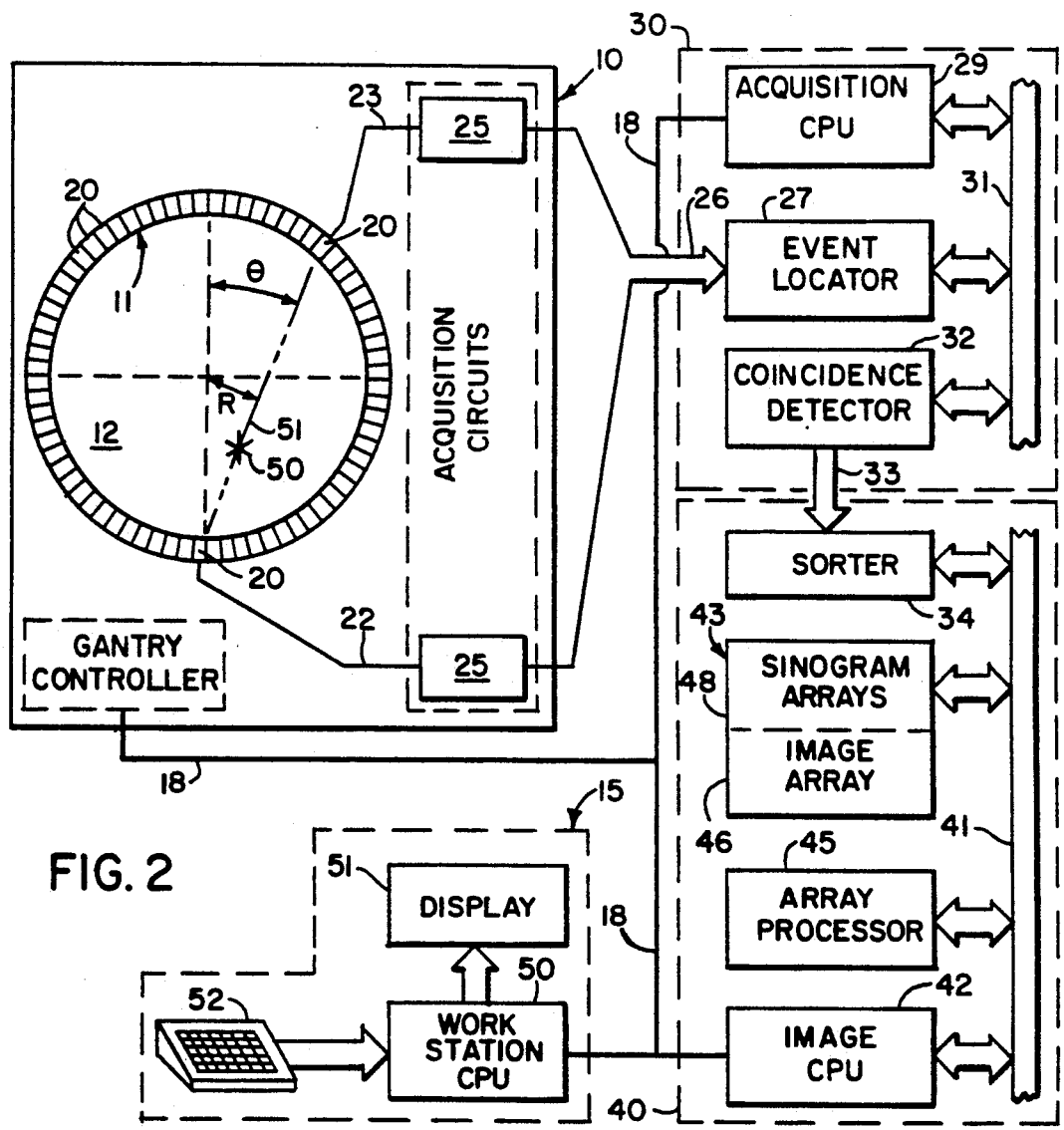
FIG. 2 is a schematic diagram of the PET scanner system of FIG. 1.
Figure 3:
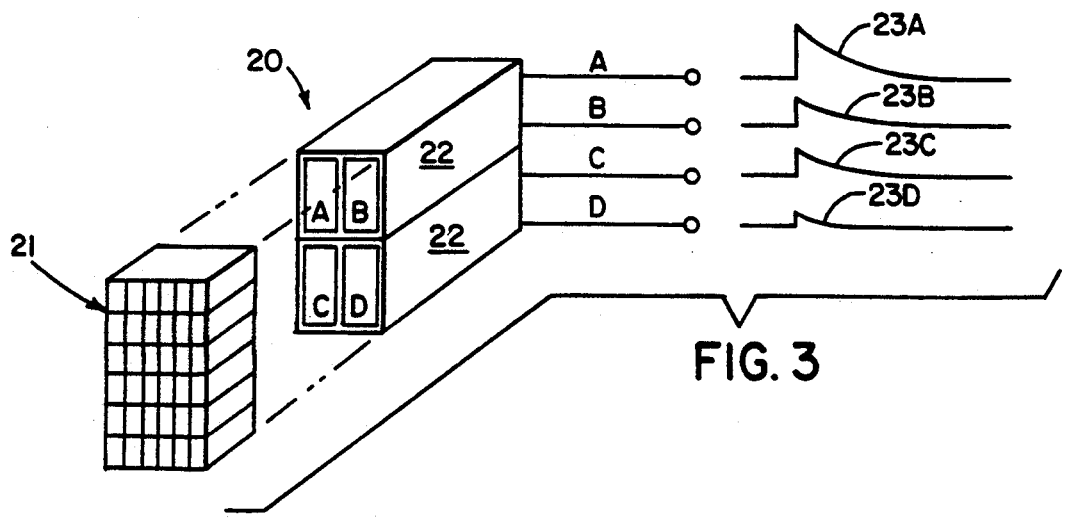
FIG. 3 is a pictorial view of a detector unit which forms part of the PET scanner system of FIG. 1.

As shown best in FIGS. 2 and 3, the detector ring 11 is comprised of 112 detector units 20. Each unit 20 includes a set of thirty-six bismuth germinate scintillator crystals 21 (abbreviated BGO) arranged in a 6×6 matrix and disposed in front of four photomultiplier tubes 22 (abbreviated PMT). Each PMT 22 produces an analog signal 23A-23D, which rises sharply when a scintillation event occurs, and then tails off exponentially with a time constant of 300 nanoseconds. The relative magnitudes of the analog signals 23A-23D is determined by the position in the 6×6 BGO matrix at which the scintillation event took place. The total magnitude of these signals is determined by the energy of the gamma ray which caused the scintillation event.

A set of acquisition circuits 25 are mounted within the gantry 10 to receive the four signals 23A-23D from each of the units 20 in the detector ring 11. In the preferred embodiment the acquisition circuits 25 determine the event coordinates within the block of BGO crystals 21 by comparing the relative signal strengths as follows:

$$x = (A+C)/(A+B+C+D); \quad (1)$$

$$z = (A+B)/(A+B+C+D) \quad (2)$$

These coordinates (x,z), along with the sum of all four signals (A+B+C+D) are then digitized and sent through a cable 26 to an event locater circuit 27 housed in a separate cabinet 28. Each acquisition circuit 25 also produces an event detection pulse (EDP) which indicates the exact moment the scintillation event took place.

Referring particularly to FIGS. 1 and 2, the event locator circuits 27 form part of a data acquisition processor 30 which periodically samples the signals produced by the acquisition circuits 25. The processor 30 has a backplane bus structure 31 which conforms with the VME standard, and an acquisition CPU 29 which controls communications on this bus 31 and links the processor 30 to the local area network 18. The event locator 27 is comprised of a set of separate circuit boards which each connect to the cable 26 and receive signals from corresponding acquisition circuits 25 in the gantry 10. The event locator 27 synchronizes the event with the operation of the processor 30 by detecting the event pulse (EDP) produced by an acquisition circuit 25, and converting it into an 8-bit time marker which indicates when within the current 250 nanosecond sample period the scintillation event took place. Also, this circuit 27 discards any detected events if the total energy of the scintillation is outside the range of 511 keV+/−20%. During each 250 nanosecond sample period, the information regarding each valid event is assembled into a set of digital numbers that indicate precisely when the event took place and the position of the BGO crystal 21 which detected the event. This event data packet is conveyed to a coincidence detector 32 which is also part of the data acquisition processor 30.

The coincidence detector 32 accepts the event data packets from the event locators 27 and determines if any a number of them are in coincidence. Coincidence is determined by a number of factors. First, the time markers in each event data packet must be within 12.5 nanoseconds of each other, and second, the locations indicated by the two event data packets must lie on a straight line which passes through the field of view (FOV) in the scanner bore 12. Events which cannot be paired are discarded, but coincident event pairs are located and recorded as a coincidence data packet that is conveyed through a serial link 33 to a sorter 34. Each coincidence data packet includes a pair of digital numbers which precisely identify the addresses of the two BGO crystals 21 that detected the event.

The sorter 34 is a circuit which forms part of an image reconstruction processor 40. The image reconstruction processor 40 is formed about a backplane bus 41 that conforms to the VME standard. An image CPU 42 controls the backplane bus 41 and it links the processor 40 to the local area network 18. A memory module 43 also connects to the backplane 41 and it stores the data used to reconstruct images. An array processor 45 also connects to the backplane 41 and it operates under the direction of the image CPU 42 to perform the image reconstruction using the data in memory module 43. The resulting image array 46 is stored in memory module 43 and is output by the image CPU 42 to the operator work station 15.

The function of the sorter 34 is to receive the coincidence data packets and generate from them memory addresses for the efficient storage of the coincidence data. The set of all projection rays that point in the same direction (θ) and pass through the scanner's field of view is a complete projection, or "view". The distance (R) between a particular projection ray and the center of the field of view locates that projection ray within the view. As shown in FIG. 2, for example, an event 50 occurs along a projection ray 51 which is located in a view at the projection angle θ and the distance R. The sorter 34 counts all of the events that occur on this projection ray (R,θ) during the scan by sorting out the coincidence data packets that indicate an event at the two BGO detector crystals lying on this projection ray. The coincidence counts are organized in memory 43 as a set of two-dimensional arrays, one for each axial image plane, and each having as one of its dimensions the projection angle θ and the other dimension the distance R. This θ by R map of the measured events is called a histrogram, or more commonly the sinogram array 48.

Coincidence events occur at random and the sorter 34 quickly determines the $\theta$ and R values from the two crystal addresses in each coincidence data packet and increments the count of the corresponding sinogram array element. The values of $\theta$ and R are calculated as follows:

$$\theta = (\phi_2 + \phi_1)/2 + 90°$$

$$R = r_0 \cos[(\phi_2 - \phi_1)/2]$$

where $\phi_1$ = angular orientation of first detector crystal;
$\phi_2$ = angular orientation of second detector crystal; and
$r_0$ = radius of detector ring.

At the completion of the scan, the sinogram array 48 stores the total number of annihilation events which occurred along each ray R in each projection, or view $\theta$.

The array processor 45 reconstructs an image from the data in the sinogram array 48. First, however, a number of corrections are made to the acquired data to correct for measurement errors such as those caused by attenuation of the gamma rays by the patient, detector gain nonuniformities, random coincidences, and integrator deadtime. Each row of the corrected sinogram array is then Fourier transformed by the array processor 45 and multiplied by a one-dimensional filter array. The filtered data is then inverse Fourier transformed and each array element is backprojected to form the image array 46. The image CPU 42 may either store the image array data on disk or tape (not shown) or output it to the operator work station 15.

The operator work station 15 includes a CPU 50, a CRT display 51 and a keyboard 52. The CPU 50 connects to the local area network 18 and it scans the keyboard 52 for input information. Through the keyboard 52 and associated control panel switches, the operator can control the calibration of the PET scanner, its configuration, and the positioning of the patient table for a scan. Similarly, the operator can control the display of the resulting image on the CRT display 51 and perform image enhancement functions using programs executed by the work station CPU 50.

Figure 4:
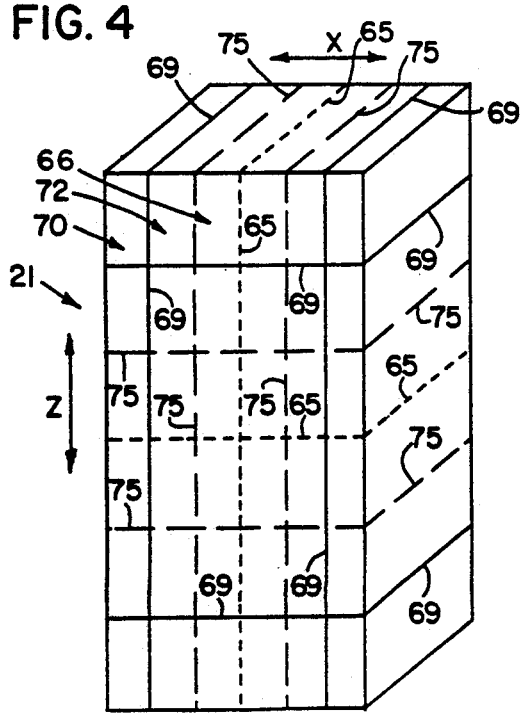
FIG. 4 is a perspective view of a preferred embodiment of the crystal array according to the present invention.

Referring particularly to FIGS. 4 and 5, the location (x, z) of the scintillations event in the 6×6 array of BGO crystals 21 is determined by the relative magnitudes of the four PMT signals as expressed above in equations (1) and (2). To enhance the accuracy of this measurement, the side surfaces of each BGO crystal in the array 21 is treated with reflective paint in a manner which will now be described in detail.

Each BGO crystal is rectangular in shape and has a front face 60 through which a gamma ray produced by an annihilation event may enter the crystal. The resulting light produced in the crystal may travel directly out the rear face (not shown) of the crystal and into the PMT 22 located immediately behind the crystal. In addition, light from the scintillation event may pass through the side surfaces of the crystal and into other crystals in the array and hence into other PMTs 22. Obviously, the light reaching other PMTs 22 by this indirect path through other crystals will not be as strong as the light reaching the PMT 22 immediately behind the crystal in which the scintillation event took place, and it is this difference which enables the scintillation location (x, z) to be determined by equations (1) and (2). The present invention relates to the treatment of the side surfaces of the crystals such that the scintillation position (x, z) can more accurately be measured with the PMT signals A, B, C and D.

Figure 5A:
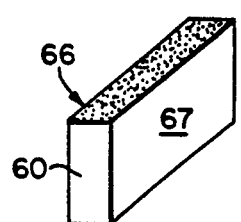
FIGS. 5A-C are perspective views of selected crystal from the array of FIG. 4.
Figure 5B:
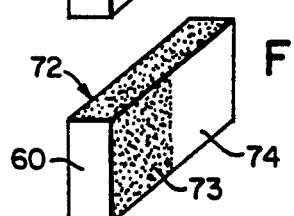

The side surfaces of the BGO crystals are treated to effect light impinging upon them in one of three ways. First, the side surface may be smooth and clear such that when it abuts a similar surface on the adjacent BGO crystal 22, a maximum possible amount of light passes through the surface and into the abutting BGO crystal 21. Such abutting surfaces are indicated in FIG. 4 by the dotted lines 65 which pass through the center of the crystal array 21. A BGO crystal 66 from the array 21 is shown in FIG. 5A, and its side surface 67 is completely clear to enable full light transmission therethrough.

Figure 5C:
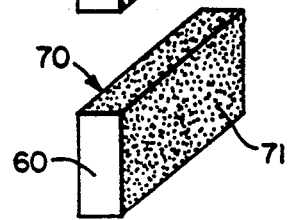

At the opposite extreme, the side surfaces of a BGO crystal may be treated to completely reflect light emanating from within the crystal. In the preferred embodiment, the entire side surface is painted with a barium sulfate reflective paint and substantially all the light is blocked from passing therethrough to the abutting BGO crystal. Such abutting crystal surfaces are indicated in FIG. 4 by the solid lines 69, and one BGO crystal 70 having its side surface 71 treated for complete reflectivity is shown in FIG. 5C. it should be noted that the outer side surface of all peripheral BGO crystals in the array 21 are treated in this manner such that light does not escape from the array 21.

The third treatment used in the preferred embodiment reflects substantially half of the light emanating from within the BGO crystal. As shown in the example BGO crystal 72 in FIG. 5B, this may be accomplished by painting bands 73 of reflective barium sulfate paint over one half the area of the crystal side surface 74. In the alternative, the entire side surface 74 may be rendered translucent by painting it with a semi-transparent paint. In either case, roughly one half of the light impinging on the side surface 74 is reflected and the other half passes through to the abutting BGO crystal. The abutting surfaces in the BGO crystal array 21 which are treated in this manner are indicated in FIG. 4 by the dashed lines 75.

Referring still to FIG. 4, it can be seen that the treatment of the BGO crystal side surfaces in accordance with the present invention varies as a function of distance from the center of the crystal array 21. That is, the reflectivity increases and the transparency decreases as a function of the distance of the abutting surfaces from the center of the crystal array 21. The abutting surfaces 65 pass through the center and have maximum transparency, the abutting surfaces 75 are disposed outward from the center and are halfway transparent, and the abutting surfaces 69 are disposed even further outward from the center and have virtually no transparency. It has been discovered that this arrangement of the BGO crystals produces signals from the four PMTs 22 which enable the x and z position of the scintillation event to be accurately located within the crystal array 21.

We claim:

1. A detector unit for a positron emission tomographic scanner, which comprises:
   an array of crystals, each crystal having:
   a) a front surface through which a gamma ray may pass and produce a scintillation event that emits light from within the crystal;

b) a rear surface through which light emanating from within the crystal may pass;

c) side surfaces which abut the side surfaces of adjacent crystals in the array and which are treated to have one of at least three different levels of transparency to the passage of light therethrough such that the transparency varies across the array of crystals, wherein the treated side surfaces which do not substantially completely transmit light therethrough are coated with a reflective pain; and an array of photomultiplier tubes disposed behind the rear surfaces of the crystals in said array of crystals, each photomultiplier tube being operable to produce an electrical signal which indicates by its magnitude the intensity of the light it receives from a scintillation event within the array of crystals.

2. The detector unit as recited in claim 1 in which the array of crystals and the array of photomultiplier tubes are two-dimensional arrays.

3. The detector unit as recited in claim 1 in which the transparency of the abutting side surfaces of the crystals in the array of crystals decreases as a function of the distance of the abutting side surfaces from the center of the crystal array.

4. The detector unit as recited in claim 3 in which the array of crystals and the array of photomultiplier tubes are two-dimensional arrays.

5. The detector unit as recited in claim 1 in which abutting side surfaces of the crystals located near the center of the array of crystals have the highest level of transparency, abutting side surfaces of the crystals located furthest from the center of the crystal array have the lowest level of transparency, and abutting side surfaces of the crystals located therebetween have a level of transparency between said highest level and said lowest level of transparency.

6. The detector unit as recited in claim 1 in which the paint is a barium sulfate reflective paint.

* * * * *